US007488610B2

(12) United States Patent
Kitajima

(10) Patent No.: US 7,488,610 B2
(45) Date of Patent: Feb. 10, 2009

(54) INSULATOR FILM CHARACTERISTIC MEASURING METHOD AND INSULATOR FILM CHARACTERISTIC MEASURING APPARATUS

(75) Inventor: Toshikazu Kitajima, Kyoto (JP)

(73) Assignee: Dainippon Screen Mfg. Co., Ltd., Kyoto (JP)

( * ) Notice: Subject to any disclaimer, the term of this patent is extended or adjusted under 35 U.S.C. 154(b) by 223 days.

(21) Appl. No.: 11/645,766

(22) Filed: Dec. 27, 2006

(65) Prior Publication Data

US 2007/0148795 A1    Jun. 28, 2007

(30) Foreign Application Priority Data

Dec. 27, 2005    (JP)    ............................. 2005-376174

(51) Int. Cl.
*H01L 21/66* (2006.01)
(52) U.S. Cl. ........................................................ 438/17
(58) Field of Classification Search .................. None
See application file for complete search history.

(56) References Cited

U.S. PATENT DOCUMENTS

| 3,394,317 | A | * | 7/1968 | Giaever ........................ 330/62 |
| 5,233,291 | A | | 8/1993 | Kouno et al. |
| 5,485,091 | A | | 1/1996 | Verkuil |
| 6,335,630 | B2 | | 1/2002 | Miller et al. |
| 6,597,193 | B2 | | 7/2003 | Lagowski et al. |
| 6,680,621 | B2 | | 1/2004 | Savtchouk et al. |
| 2004/0019442 | A1 | | 1/2004 | Kitajima et al. |

* cited by examiner

*Primary Examiner*—Charles D. Garber
*Assistant Examiner*—Andre' C Stevenson
(74) *Attorney, Agent, or Firm*—McDermott Will & Emery LLP

(57) ABSTRACT

A method is for measuring the characteristics of an insulator film (inner charge amount, film thickness, relative dielectric constant, surface voltage change due to a surface adsorbed substance, etc.) formed on a surface of a semiconductor substrate in a non-contact manner. This method includes: a step of measuring a measured surface voltage characteristic in a non-contact manner with respect to the insulator film; a step of provisionally setting a plurality of inner charge amounts; a step of calculating, with respect to each of the plurality of inner charge amounts, a theoretical surface voltage characteristic; a step of obtaining, with respect to each of the theoretical surface voltage characteristics, a mean value difference which is a difference between a surface voltage mean value of the measured surface voltage characteristics and a surface voltage mean value of the theoretical surface voltage characteristics, so that the mean value difference is set as a surface voltage change due to a surface adsorbed substance; a step of calculating, with respect to each of the theoretical surface voltage characteristics, a deviation of the measured surface voltage characteristic with respect to the corrected surface voltage characteristic; and a step of determining a set-point for the inner charge amount corresponding to the theoretical surface voltage characteristic which minimizes the deviation.

8 Claims, 9 Drawing Sheets

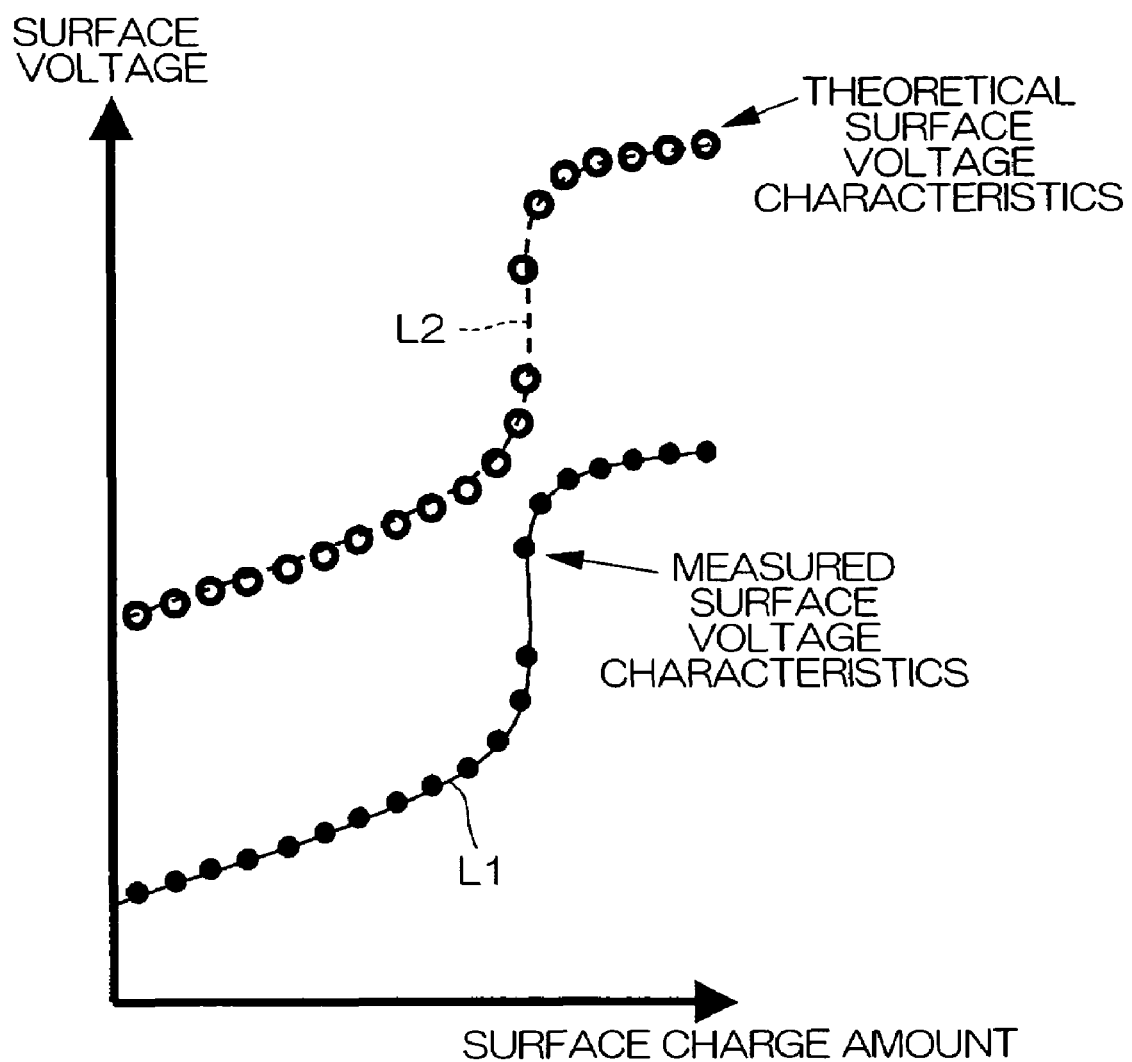

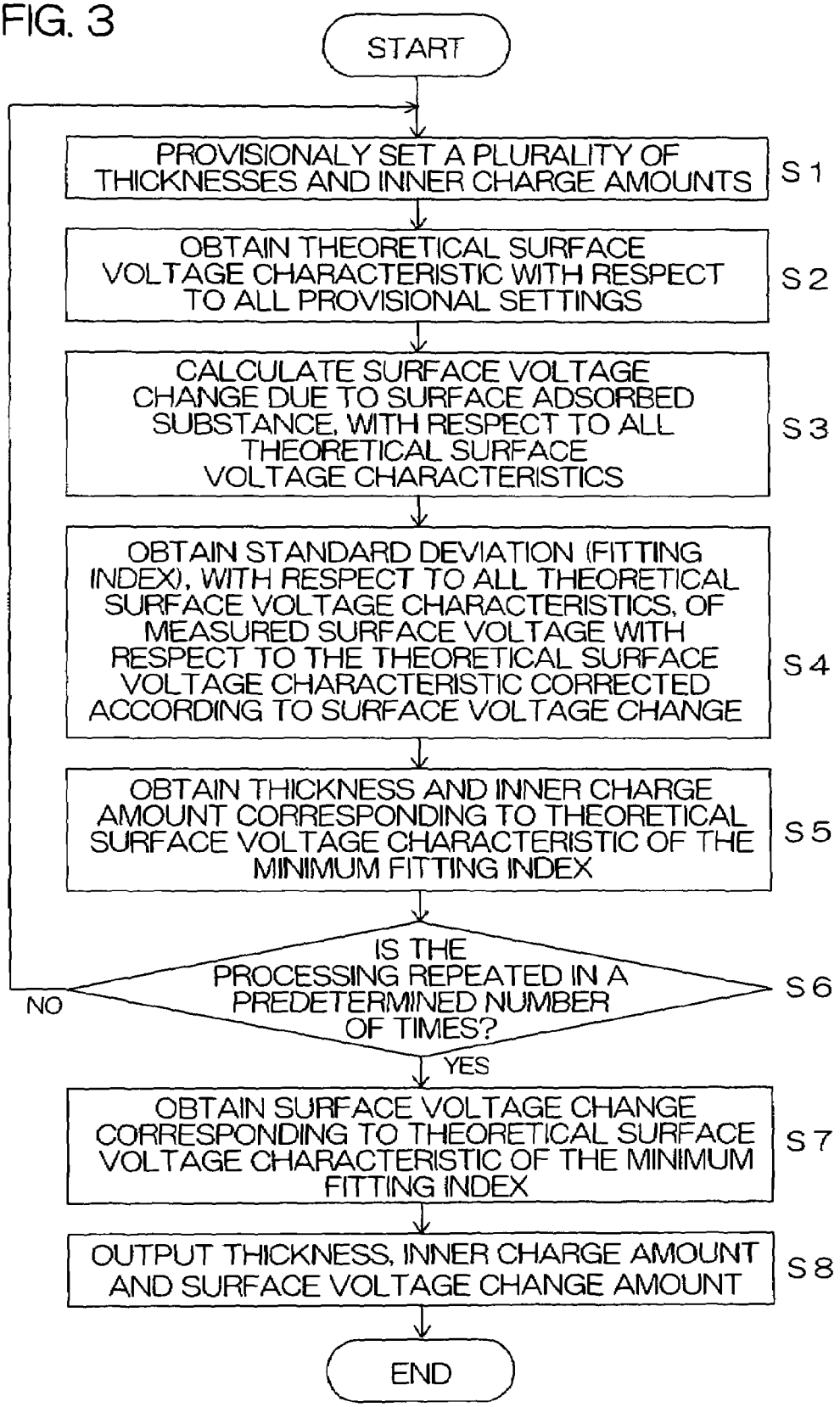

INSULATOR FILM CHARACTERISTIC MEASURING METHOD AND INSULATOR FILM CHARACTERISTIC MEASURING APPARATUS

BACKGROUND OF THE INVENTION

1. Field of the Invention

The present invention relates to a method and apparatus for measuring the characteristics of an insulated film (inner charge amount, film thickness, relative dielectric constant, etc.) formed on a semiconductor substrate.

2. Description of Related Art

In the semiconductor device production process, various films including an insulator film are formed on a semiconductor substrate. The characteristics of the insulator film have a great influence on the characteristics of the semiconductor device. It is therefore inevitable to evaluate the characteristics of the insulator film during the semiconductor device production process.

With the progress of semiconductor device integration technology, the type and thickness of an insulator film to be used have undergone a change. This has consequently changed the insulator film evaluation method. For example, there have been instances where an optical method (e.g., ellipsometry) is used as a method of measuring the thickness of an insulator film. Such an optical measuring method may not always be accurate under the influence of an organic substance attached to the insulator film surface. Therefore, attention is now placed on an electric film thickness measuring method directly related to the device operation.

With the change in the type of an insulator film, the relative dielectric constant of the insulator film becomes an important parameter. It is therefore required to measure more accurately the relative dielectric constant of the insulator film.

The insulator film thickness can be obtained when the surface charge amount, the surface voltage and the relative dielectric constant are known. The relative dielectric constant of an insulator film can be obtained when the surface charge amount, the surface voltage and the film thickness are known. Accordingly, when either the film thickness or the relative dielectric constant is known in addition to the surface charge amount and the surface voltage, the other can be obtained.

In order to stably form a high-quality insulator film, it is important to control the inner charge amount of an insulator film. It is therefore required to measure more accurately the inner charge amount of the insulator film.

There is a method of measuring the film thickness, relative dielectric constant, or inner charge amount of an insulator film, in which electrodes are formed on the surface of the insulator film. However, this method is not a preferable measuring method, because this is a destructive test and includes a number of processing steps. There can be also considered using mercury as electrodes. However, the mercury is detrimental to the human body and is therefore troublesome to deal with. Besides, since mercury is a liquid, which does not stabilize its electrode area, so that an accurate measurement cannot be achieved. Furthermore, in either event, when the electrodes are formed on the surface of the insulator film, this involves the likelihood that an electric current leaks through the insulator film at the time of measurement, making the measurement inaccurate.

It is therefore desired to establish a method of measuring, in a non-contact manner, the insulator film characteristics such as the thickness, relative dielectric constant, or inner charge amount of an insulator film. Such a measuring method proposes a technique of measuring the surface charge amount and surface voltage of an insulator film at the time when the surface of the insulator film is charged, and of obtaining the thickness or relative dielectric constant of the insulator film based on the values thus measured (United States Patent Application Publication No. US2004/0019442A1). However, the measurement of other physical quantities such as inner charge amount, surface voltage change due to a surface adsorbed substance, or substrate carrier concentration has not been proposed.

Another earlier technique of measuring the thickness of an insulator film is disclosed in U.S. Pat. No. 5,485,091. However, with this earlier technique, the relative dielectric constant, inner charge amount, surface voltage change due to a surface adsorbed substance, or substrate carrier concentration of an insulator film cannot be obtained.

In recent years, with the progress of semiconductor device integration technology, there has been a new problem of adsorption of an organic substance on the insulator film surface. More specifically, in a clean room, there exists a large amount of organic substances detached from resins or the like. These organic substances are adsorbed on the insulator film surface, thereby causing a problem at various processing steps. Therefore, it is important to control such that no organic substance generates in the substrate processing apparatus. In order to achieve this, it is required to measure the adsorption of an organic substance on the substrate surface. The amount of the organic substance in an atmosphere or on an insulator film can be measured by chemical analysis. However, the measurement by chemical analysis is time consuming. Accordingly, when the chemical analysis is applied, particularly to the measurement of the organic substance attached to the surface of an insulator film on a substrate, organic substance contamination associated with in-line cannot be measured.

Therefore, a need exists for a convenient measuring technique capable of electrically measuring the adsorption of an organic substance on an insulator film.

The insulator film surface voltage can be measured with a Kelvin probe. However, in light of the influence by the inner charge amount or surface charge amount of an insulator film, the measurement of the surface voltage change due to a surface adsorbed substance attached to the insulator film surface has not been performed.

SUMMARY OF THE INVENTION

It is an object of the present invention to provide an insulator film characteristic measuring method and an insulator film characteristic measuring apparatus, each of which is capable of accurately measuring the characteristics of an insulator film formed on a surface of a semiconductor substrate in a non-contact manner.

It is a specific object of the present invention to provide a method and an apparatus capable of accurately measuring the inner charge amount of an insulator film formed on a surface of a semiconductor substrate in a non-contact manner.

It is a further specific object of the present invention to provide a method capable of accurately measuring the thickness of an insulator film formed on a surface of a semiconductor substrate in a non-contact manner.

It is another specific object of the present invention to provide a method capable of accurately measuring the relative dielectric constant of an insulator film formed on a surface of a semiconductor substrate in a non-contact manner.

It is a still further specific object of the present invention to provide a method capable of accurately measuring the carrier concentration of a semiconductor substrate on which an insulator film is formed in a non-contact manner.

It is a still further specific object of the present invention to provide a method and an apparatus capable of accurately measuring the surface voltage change due to a surface adsorbed substance attached to a surface of an insulator film formed on a surface of a semiconductor substrate in a non-contact manner.

The present invention provides an insulator film characteristic measuring method for measuring the characteristics of an insulator film formed on a surface of a semiconductor substrate in a non-contact manner with respect to the insulator film. This method comprises: a surface voltage characteristic measuring step for measuring a measured surface voltage characteristic which is a surface voltage characteristic with respect to a surface charge amount of the insulator film in a non-contact manner with respect to the insulator film; a provisional setting step for provisionally setting a plurality of inner charge amounts; a theoretical surface voltage characteristic calculation step of calculating, with respect to each of the plurality of inner charge amounts provisionally set, a theoretical surface voltage characteristic which is a theoretical characteristic of the surface voltage (surface voltage in the absence of a surface adsorbed substance on the insulator film surface) with respect to the surface charge amount of the insulator film; a step for obtaining, with respect to each of the theoretical surface voltage characteristics, a mean value difference which is a difference between a surface voltage mean value obtained based on the measured surface voltage characteristics and a surface voltage mean value obtained based on the theoretical surface voltage characteristics, so that the mean value difference is set as a surface voltage change due to a surface adsorbed substance which is adsorbed on the insulator film surface (difference between the insulator film surface voltage in the absence of an adsorbed substance and the insulator film surface voltage in the presence thereof); a step for calculating, with respect to each of the theoretical surface voltage characteristics, a deviation (for example, standard deviation) of the measured surface voltage characteristic with respect to the corrected surface voltage characteristic which is obtained by correcting the theoretical surface voltage characteristic based on the surface voltage change; and a minimum deviation set-point determining step of determining a set-point for the inner charge amount corresponding to the theoretical surface voltage characteristic which minimizes the deviation.

In the present invention, the surface voltage characteristic with respect to the surface charge amount of an insulator film is measured in a non-contact manner with respect to the insulator film. On the other hand, a plurality of inner charge amount values of the insulator film are provisionally set. With respect to each of the plurality of the inner charge amounts, a theoretical characteristic of the surface voltage (theoretical surface voltage characteristic) is calculated. Then, there is obtained a difference (mean value difference) between the surface voltage mean value obtained based on the measured surface voltage characteristics and the surface voltage mean value obtained based on the theoretical surface voltage characteristics. Based on the mean value difference, a surface voltage change due to an adsorbed substance on the insulator film surface is calculated. When the theoretical surface voltage characteristic is corrected based on the surface voltage change, if the inner charge amount thus provisionally set is a true value, the theoretical surface voltage characteristic after the correction is considered to nearly fit with the measured surface voltage characteristic. Then, there is obtained a deviation of the measured surface voltage characteristic with respect to the theoretical surface voltage characteristic after the correction, and is found a set-point for the inner charge amount corresponding to the theoretical surface voltage characteristic which minimizes the deviation. Thus, by the non-contact measurement for an insulator film, the inner charge amount of the insulator film can be obtained.

In one embodiment of the present invention, the provisional setting step includes a step of setting a plurality of the thicknesses and inner charge amounts of the insulator film; the theoretical surface voltage characteristic calculation step includes a step of calculating a theoretical surface voltage characteristic with respect to a plurality (preferably all) of combinations of each of the thicknesses and inner charge amounts thus provisionally set; and the minimum deviation set-point determining step includes a step of determining a set-point group comprising a thickness and an inner charge amount, each corresponding to the theoretical surface voltage characteristic which minimizes the deviation.

According to this method, a plurality of the thicknesses and inner charge amounts of an insulator film are provisionally set. The theoretical surface voltage characteristic is calculated with respect to a plurality (preferably all) of combinations of each of the thicknesses and inner charge amounts thus provisionally set. Among the theoretical surface voltage characteristics thus calculated, there is found one which minimizes the deviation of the theoretical surface voltage characteristic after the correction with respect to the measured surface voltage characteristic, and is then extracted a set-point group comprising a thickness and an inner charge amount, each corresponding to the deviation. This extracted group values of the thickness and inner charge correspond to true values of an insulator film formed on a surface of a semiconductor substrate. Thus, by the non-contact measurement for an insulator film, the thickness and the inner charge amount can be measured.

In a further embodiment of the present invention, the provisional setting step includes a step of setting a plurality of the inner charge amounts and substrate carrier concentrations; the theoretical surface voltage characteristic calculation step includes a step of calculating a theoretical surface voltage characteristic with respect to a plurality (preferably all) of combinations of each of the inner charge amounts and substrate carrier concentrations thus provisionally set; and the minimum deviation set-point determining step includes a step of determining a set-point group comprising an inner charge amount and a substrate carrier concentration, each corresponding to the theoretical surface voltage characteristic which minimizes the deviation.

According to this method, a plurality of the inner charge amounts and substrate carrier concentrations are provisionally set. The theoretical surface voltage characteristic is calculated with respect to a plurality (preferably all) of combinations of each of the inner charge amounts and substrate carrier concentrations thus provisionally set. Then, the surface voltage change is calculated based on the difference between the mean value of the theoretical surface voltage characteristics thus calculated and the mean value of the measured surface voltage characteristics. The deviation of the measured surface voltage characteristic is obtained with respect to the theoretical surface voltage characteristics corrected according to the surface voltage change thus calculated, and there is found the theoretical surface voltage characteristic which minimizes the deviation. The set-points for the inner charge amount and substrate carrier concentration, each corresponding to the theoretical surface voltage characteristic can be regarded as true values thereof. Thus, by the non-contact measurement for an insulator film, the inner charge amount and the substrate carrier concentration can be measured.

In another embodiment of the present invention, the provisional setting step includes a step of setting a plurality of the thicknesses, inner charge amounts and substrate carrier concentrations of the insulator film; the theoretical surface voltage characteristic calculation step includes a step of calculating a theoretical surface voltage characteristic with respect to a plurality (preferably all) of combinations of each of the thicknesses, inner charge amounts and substrate carrier concentrations thus provisionally set; and the minimum deviation set-point determining step includes a step of determining a set-point group comprising a thickness, an inner charge amount and a substrate carrier concentration, each corresponding to the theoretical surface voltage characteristic which minimizes the deviation.

According to this method, a plurality of the thicknesses, inner charge amounts and substrate carrier concentrations of an insulator film are provisionally set. The theoretical surface voltage characteristic is calculated with respect to a plurality (preferably all) of combinations of each of the values. The surface voltage change is obtained with respect to all the theoretical surface voltage characteristics thus calculated. Then, there is found a combination of the provisional set-points corresponding to the theoretical surface voltage characteristic which minimizes the deviation of the measured surface voltage characteristic with respect to the theoretical surface voltage characteristics corrected according to the surface voltage change thus obtained. The values of this combination correspond to true values for a semiconductor substrate and an insulator film to be measured. Thus, by the non-contact measurement, the thickness, the inner charge amount and the substrate carrier concentration of an insulator film can be obtained.

In a still further embodiment of the present invention, the provisional setting step includes a step of setting a plurality of the relative dielectric constants and inner charge amounts of the insulator film; the theoretical surface voltage characteristic calculation step includes a step of calculating a theoretical surface voltage characteristic with respect to a plurality (preferably all) of combinations of each of the relative dielectric constants and inner charge amounts thus provisionally set; and the minimum deviation set-point determining step includes a step of determining a set-point group comprising a relative dielectric constant and an inner charge amount, each corresponding to the theoretical surface voltage characteristic which minimizes the deviation.

According to this method, a plurality of the relative dielectric constants and inner charge amounts of an insulator film are provisionally set and the theoretical surface voltage characteristic is obtained with respect to all the combinations thereof. Then, there is found a set-point combination which minimizes the deviation of the measured surface voltage characteristic with respect to the theoretical surface voltage characteristic corrected according to the surface voltage change. The set-points of this combination correspond to the relative dielectric constant and the inner charge amount of an insulator film formed on a semiconductor substrate. Thus, by the non-contact measurement, the relative dielectric constant and the inner charge amount of an insulator film can be measured.

In a still further embodiment of the present invention, the provisional setting step includes a step of setting a plurality of the relative dielectric constants, inner charge amounts and substrate carrier concentrations of the insulator film; the theoretical surface voltage characteristic calculation step includes a step of calculating a theoretical surface voltage characteristic with respect to a plurality (preferably all) of combinations of each of the relative dielectric constants, inner charge amounts and substrate carrier concentrations thus provisionally set; and the minimum deviation set-point determining step includes a step of determining a set-point group comprising a relative dielectric constant, an inner charge amount and a substrate carrier concentration, each corresponding to the theoretical surface voltage characteristic which minimizes the deviation.

According to this method, a plurality of the relative dielectric constants, inner charge amounts and substrate carrier concentrations of an insulator film are provisionally set. The theoretical surface voltage characteristic is calculated with respect to a plurality (preferably all) of combinations of each of the values, and the deviation of the measured surface voltage characteristic is obtained with respect to the theoretical surface voltage characteristic corrected according to the surface voltage change. The provisional set-points of the group, each corresponding to the theoretical surface voltage characteristic which minimizes the deviation thus obtained, can be regarded as true values representing the characteristics of an semiconductor substrate and insulator film. Thus, by the non-contact measurement for an insulator film, the relative dielectric constant, the inner charge amount and the substrate carrier concentration can be measured.

The method mentioned above may further include a step of extracting a surface voltage change obtained so as to correspond to the theoretical surface voltage characteristic associated with the set-points determined according to the minimum deviation set-point determining step.

In this method, there is extracted the surface voltage change corresponding to the theoretical surface voltage characteristic associated with the set-points which minimize the deviation, among the plurality of the theoretical surface voltage characteristics. The surface voltage thus extracted finally corresponds to a true value of the surface voltage change due to a surface adsorbed substance in the insulator film on the semiconductor substrate. Thus, by the non-contact measurement for an insulator film, the surface voltage change due to a surface adsorbed substance can be measured.

The insulator film characteristic measuring apparatus of the present invention is an apparatus for measuring the characteristics of an insulator film formed on a surface of a semiconductor substrate in a non-contact manner with respect to the insulator film. This apparatus comprises: a surface voltage characteristic measuring unit for measuring a measured surface voltage characteristic which is a characteristic of a surface voltage with respect to a surface charge amount of the insulator film in a non-contact manner with respect to the insulator film; a provisional setting unit for provisionally setting a plurality of inner charge amounts; a theoretical surface voltage characteristic calculation unit for calculating, with respect to each of the plurality of inner charge amounts provisionally set, a theoretical surface voltage characteristic which is a theoretical characteristic of the surface voltage with respect to the surface charge amount of the insulator film; a surface voltage change operation unit for obtaining, with respect to each of the theoretical surface voltage characteristics, a mean value difference which is a difference between a surface voltage mean value obtained based on the measured surface voltage characteristics and a surface voltage mean value obtained based on the theoretical surface voltage characteristics, so that the mean value difference is set as a surface voltage change due to a surface adsorbed substance which is adsorbed on the insulator film surface; a deviation operation unit for calculating, with respect to each of the theoretical surface voltage characteristics, a deviation of the measured surface voltage characteristic with respect to the corrected surface voltage characteristic which is obtained by correcting the theoretical surface voltage characteristic according to the surface voltage change; and a minimum deviation set-point determining unit for determining a set-point for the inner charge amount corresponding to the theoretical surface voltage characteristic which minimizes the deviation.

These and other features, objects, advantages and effects of the present invention will be more fully apparent from the following detailed description set forth below when taken in conjunction with the accompanying drawings.

BRIEF DESCRIPTION OF THE DRAWINGS

FIG. 2 is an example of the surface voltage characteristic which has been measured (measured surface voltage characteristic) with respect to the surface charge amount.

FIG. 3 is a flow chart for explaining an example of a process to be executed by a control unit at the time when the characteristics of an insulator film formed on a wafer are obtained, with the use of the measured surface voltage characteristic and a large number of theoretical surface voltage characteristics, the flow chart illustrating a process in the case where the thickness, the inner charge amount and the surface voltage change due to a surface adsorbed substance are not known.

DETAILED DESCRIPTION OF PREFERRED EMBODIMENTS

Figure 1:
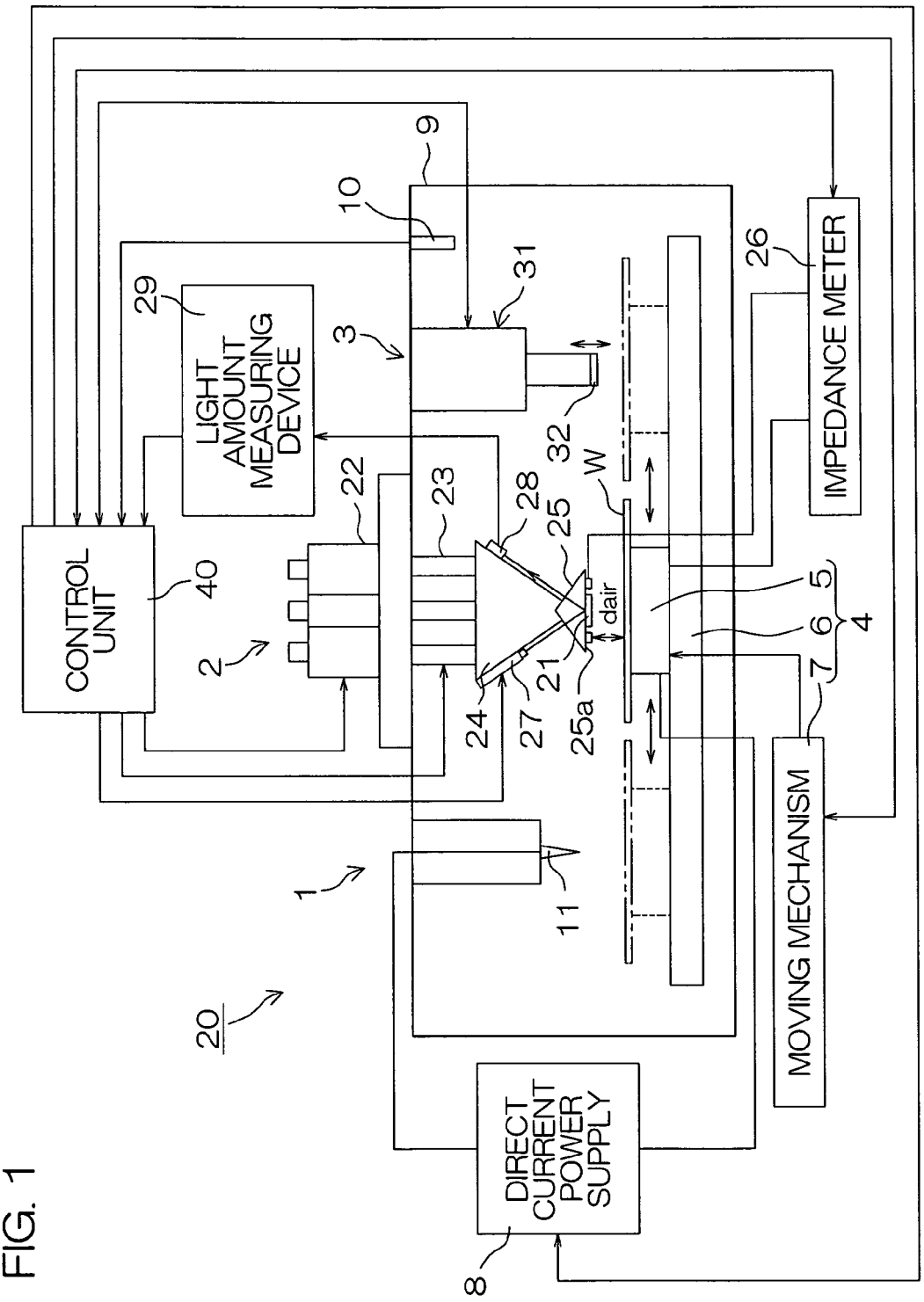
FIG. 1 is a schematic front view of an insulator film characteristic measuring apparatus according to one embodiment of the present invention.

FIG. 1 is a schematic front view of an insulator film characteristic measuring apparatus according to one embodiment of the present invention. The insulator film characteristic measuring apparatus 20 is arranged to measure the thickness, relative dielectric constant or the like of an insulator film formed on a surface of a wafer W as an example of a semiconductor substrate, and comprises a charging processing unit 1, a C-V measuring unit 2 and a surface voltage measuring unit 3 in a chamber 9. In this embodiment, the charging processing unit 1, the C-V measuring unit 2 and the surface voltage measuring unit 3 are successively linearly disposed along the horizontal direction in FIG. 1. The wafer W is arranged to be moved, by a loader 4, among a charging processing position at the charging processing unit 1, a C-V measuring position at the C-V measuring unit 2, and a surface voltage measuring position at the surface voltage measuring unit 3.

Disposed in the chamber 9 is a temperature sensor 10 for measuring the ambient temperature in the chamber 9. Provision is made such that an output of the temperature sensor 10 is entered to a control unit 40 having a basic form of a computer (e.g., a personal computer).

The loader 4 comprises a holding stand 5 for substantially horizontally holding a wafer W, a rail 6 for supporting and linearly guiding the holding stand 5 in a substantially horizontal direction, and a moving mechanism 7 for moving the holding stand 5 along the rail 6. The holding stand 5 is arranged to hold a wafer W, for example, by vacuum-suction of the underside of the wafer W. That portion of the holding stand 5 arranged to come in contact with the wafer W is made of an electric conductor and serves as a contact electrode.

The charging processing unit 1 is arranged to charge a wafer W by corona discharge, and has a needle 11 for applying a voltage. Each of the needle 11 and the holding stand 5 is connected to a direct current power supply 8. Provision is made such that the wafer W is opposite to the needle 11 at the charging processing position.

Provision is made such that when the wafer W is located in the charging processing position, a direct current voltage is applied between the needle 11 and the holding stand 5 by the direct current power supply 8 to generate corona discharge between the needle 11 and the wafer W, enabling to charge the insulator film formed on the wafer W surface. The direct current power supply 8 can reverse the polarity of the voltage to apply, thus enabling to charge the wafer W positively or negatively.

The C-V measuring unit 2 is arranged to measure a surface charge amount of a wafer W by a C-V measurement (capacitance-voltage measurement) to be discussed later. The C-V measuring unit 2 comprises a base 24, a trigonal prism 25 attached to the lower portion of the base 24, and a measuring electrode 21 attached to the bottom face 25a of the prism 25. The prism 25 is substantially horizontally disposed with one of the lateral sides of the trigonal shape turned down. This side is hereinafter referred to as "the bottom face 25a". Each of the measuring electrode 21 and the holding stand 5 is connected to an impedance meter 26. Provision is made such that a combined capacitance between the measuring electrode 21 and the holding stand 5 can be measured while applying a bias voltage between the measuring electrode 21 and the holding stand 5. The impedance meter 26 is arranged to change the magnitude of the bias voltage. Thus, a C-V measurement can be performed.

The base 24 is connected to a stepping motor 22 through a piezoelectric actuator 23, and is arranged to be vertically moved by the stepping motor 22 and the piezoelectric actuator 23. Provision is made such that the wafer W at the C-V measuring position is opposite to the measuring electrode 21. When the wafer W is located in the C-V measuring position, the gap between the wafer W and the measuring electrode 21 can be adjusted roughly by the stepping motor 22, and finely by the piezoelectric actuator 23. The piezoelectric actuator 23 may have a piezoelectric element made of, for example, PZT (lead zirconate titanate).

Attached to the base 24 are a laser oscillator 27 for emitting a laser light and a light receiving sensor 28. Provision is made such that a laser light emitted from the laser oscillator 27 is totally reflected by the bottom face 25a of the prism 25, and received by the light receiving sensor 28. The light receiving sensor 28 is connected to a light amount measuring device 29 for measuring the light amount of the laser light received by the light receiving sensor 28.

The light amount measured by the light amount measuring device 29 is effected by the tunnel effect of the laser light reflected by the bottom face 25a of the prism 25. Accordingly, the gap $d_{air}$ between the wafer W and the measuring electrode 21 can be measured. The principle of this gap measuring method is detailed in U.S. Pat. No. 5,233,291. Under certain conditions, the logarithm log $R_t$ of the transmission factor $R_t$ of the laser light at the bottom face 25a and the gap $d_{air}$ are regarded to be in proportion to each other. When the reflectance is known, the transmission factor $R_t$ can be obtained. Accordingly, when the reflectance is obtained from the light amount of the laser light measured by the light amount measuring device 29, the gap $d_{air}$ can be obtained.

Provision is made such that output signals of the light amount measuring device 29 and the impedance meter 26 are entered to the control unit 40. At the control unit 40, a flat band voltage can be obtained from the C-V measurement result, and the surface charge amount Q given to the insulator film surface by the charging processing can be obtained from the flat band voltages before and after the charging processing, and from the gap $d_{air}$.

The surface voltage measuring unit 3 has a Kelvin probe 31 having an electrode 32. Provision is made such that the wafer W at the surface voltage measuring position is opposite to the Kelvin probe 31. The Kelvin probe 31 is arranged to vertically vibrate the electrode 32 and to apply a voltage thereto. When the electrode 32 is vibrated at the time a wafer W of which insulator film surface has been charged is located in the surface voltage measuring position, an electric charge undergoing a change based on the vibrational frequency of the electrode 32 is induced to the electrode 32. This electric charge can be negated by applying a suitable voltage to the electrode 32. Based on the voltage at this time, the wafer W surface voltage can be obtained. Provision is made such that an output signal of the Kelvin probe 31 is entered to the control unit 40.

The operations of the moving mechanism 7, the direct current power supply 8, the impedance meter 26, the laser oscillator 27 and the Kelvin probe 31 are to be controlled by the control unit 40.

FIG. 2 shows an example of the surface voltage characteristic with respect to the surface charge amount, and the surface voltage characteristic which has been measured (measured surface voltage characteristics) is shown by a curve L1. The above measured surface voltage characteristics can be obtained, in the arrangement shown in FIG. 1, by giving various surface charge amounts to a wafer W by the charging processing unit 1 to measure the C-V characteristics at the C-V measuring unit 2, and by measuring the surface voltage (insulator film surface voltage) of the wafer W at the surface voltage measuring unit 3 (surface voltage characteristic measurement step, surface voltage characteristic measurement unit). More specifically, the measured surface voltage characteristics as described above can be obtained by correlating the surface charge amount calculated based on the C-V characteristic measurement result with the measurement result by the surface voltage measuring unit 3 at the control unit 40.

However, in the case where the charged amount can accurately be controlled at the charging processing unit 1, the surface charge amount measurement is not required. Accordingly, provision may be made such that the measured surface voltage characteristics are obtained by correlating the charged amount thus controlled with the surface voltage measured by the surface voltage measuring unit 3.

On the other hand, the control unit 40 operates such that a theoretical value of the surface voltage characteristic with respect to the surface charge amount of an insulator film formed on a wafer W surface (theoretical surface voltage characteristic: an example thereof is shown by a curve L2 in FIG. 2) is obtained by calculation. At this time, the control unit 40 sets parameters (such as the thickness and inner charge amount of an insulator film) necessary to calculate the theoretical surface voltage characteristic to various values, and calculates a plurality of the theoretical surface voltage characteristics. Among the plurality of the theoretical surface voltage characteristics thus calculated, there is found one which is the most approximate to the measured surface voltage characteristic, and the parameter corresponding to the theoretical surface voltage characteristic thus found is set as a characteristic value (true value) of an insulator film formed on a wafer W.

The insulator film surface potential $V_{surf}$ is expressed by the following formula (1):

$$V_{surf} = \phi_s + V_{ins} + \phi_{ref} - \phi_{sub} + \phi_{org} \tag{1}$$

where $\phi_s$ represents the surface potential of the insulator film; $V_{ins}$ represents the potential applied to the insulator film; $\phi_{ref}$ represents the work function of the surface voltage reference sample; $\phi_{sub}$ represents the work function of the semiconductor substrate (wafer W); and $\phi_{org}$ represents the surface voltage change due to a surface adsorbed substance attached to the insulator film surface.

When the semiconductor substrate is P-type, the surface potential $\phi_s$ can be obtained according to the following formula (2):

$$Q_s = \mp \frac{\sqrt{2}\,\varepsilon_s kT}{qL_D} F\!\left(\beta\phi_s, \left(\frac{n_i}{N_{sub}}\right)^2\right) \tag{2}$$

$$F\!\left(\beta\phi_s, \left(\frac{n_i}{N_{sub}}\right)^2\right) = \left[(e^{-\beta\phi_s} + \beta\phi_s - 1) + \left(\frac{n_i}{N_{sub}}\right)^2 (e^{\beta\phi_s} - \beta\phi_s - 1)\right]^{1/2} \tag{3}$$

$$L_D = \sqrt{\frac{kT\varepsilon_s}{q^2 N_{sub}}} \tag{4}$$

where $Q_s$ is the charge amount induced on the substrate side and is the value obtained by adding the surface charge amount to the inner charge amount and reversing the sign of the sum. And, $\varepsilon_s$ is the dielectric constant of the semiconductor substrate; k is a Boltzmann constant; T is a temperature; q is an elementary electric charge; $L_D$ is a Debye length; $n_i$ is an intrinsic carrier concentration; $N_{sub}$ is the substrate carrier concentration; and $\beta$ is q/kT. As to the sign "±" in the formula (2), either "plus" or "minus" is determined depending on the sign of $Q_s$.

The surface potential $\phi_s$ is the value for which the above formula (2) holds. Newton's method or the like can be used in the calculation. Therefore, according to the method, the surface potential $\phi_s$ can be obtained based on the surface charge amount and the inner charge amount. A reference value may be used as the dielectric constant $\in_s$ of the semiconductor substrate. The input value is used as the substrate carrier concentration.

Assuming that the inner charge amount exists in the vicinity of the interface of an insulator film, the potential applied to the insulator film $V_{ins}$ is expressed by the following formula (5):

$$V_{ins} = \frac{d_{ins}}{\varepsilon_{ins}} Q_{surf} \quad (5)$$

where $d_{ins}$ is the insulator film thickness, $\in_{ins}$ is the dielectric constant of the insulator film, $Q_{surf}$ is the surface charge amount. A reference value or the like can also be used as the dielectric constant $\in_{ins}$ of the insulator film.

A reference value or a value obtained based on an experiment can be used as the work function $\phi_{ref}$ of the surface voltage reference sample. The surface voltage obtained by the formula (1) is the value in the case where the surface voltage at the time of measuring the above surface voltage reference sample, is set to zero. Generally, a surface voltage meter has a zero adjustment function. When the zero adjustment is conducted during the measurement of the surface voltage reference sample, the measured surface voltage is expressed by the formula (1).

The semiconductor substrate work function $\phi_{sub}$ is expressed by the following formulas (6) and (7):

$$\phi_{sub} = \frac{\chi}{q} + \frac{E_g/2}{q} \pm \phi_b \quad (+:P \text{ type}, -:N \text{ type}) \quad (6)$$

$$\phi_b = \frac{kT}{q} \ln \frac{N_{sub}}{n_i} \quad (7)$$

where $\chi$ is the electron affinity of the semiconductor substrate, $E_g$ is the semiconductor substrate band gap, $\phi_b$ is the difference between the Fermi level and the intrinsic Fermi level, and reference values may be used as the electron affinity $\chi$ and the band gap $E_g$.

Figure 4A:
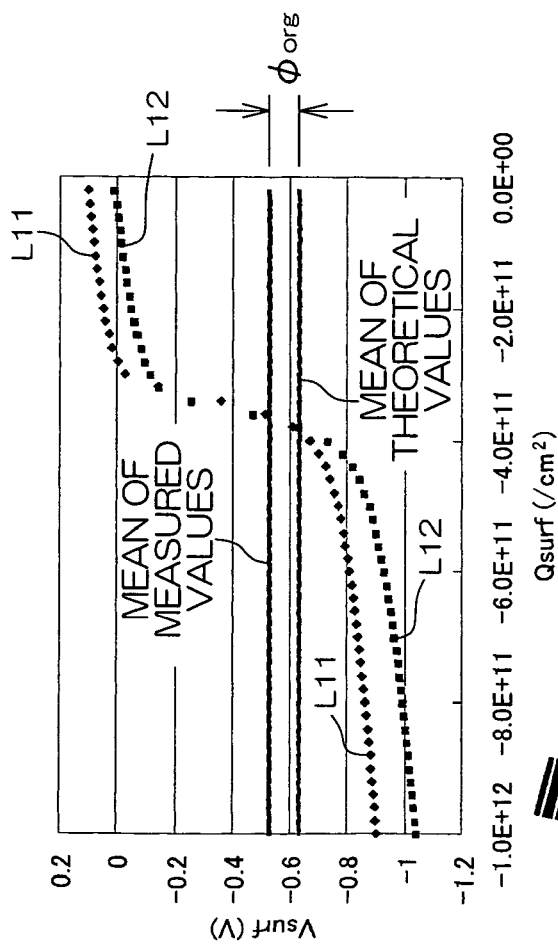
FIGS. 4A, 4B and 4C are views for explaining an image of a process to be executed by a control unit at the time of obtaining the characteristics of an insulator film.
Figure 4C:
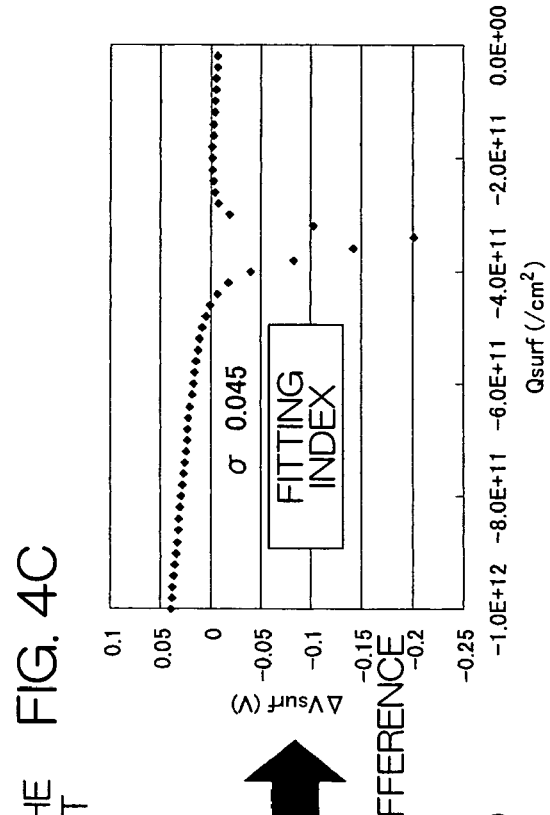
Figure 4B:
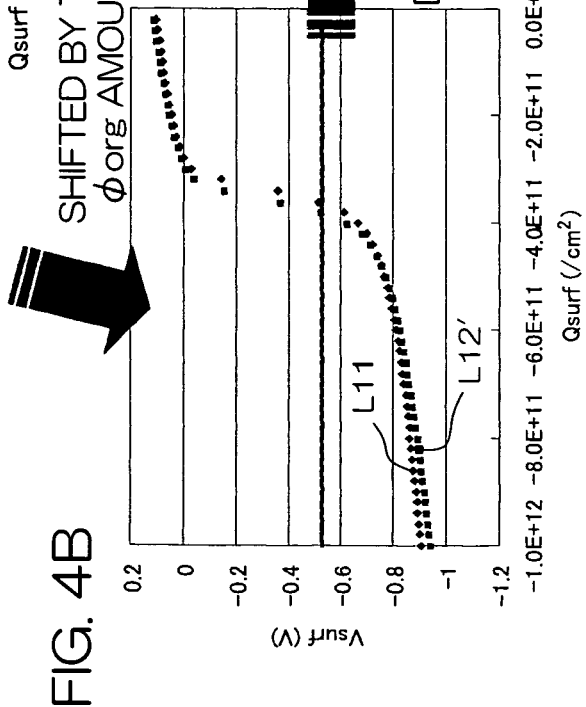

FIG. 3 is a flow chart for explaining an example of a process to be executed by a control unit 40 at the time when the characteristics of an insulator film formed on a wafer W are obtained, with the use of the measured surface voltage characteristic and a large number of theoretical surface voltage characteristics, and illustrating a process in the case where the thickness, the inner charge amount and the surface voltage change due to a surface adsorbed substance are not known. FIGS. 4A, 4B and 4C are views illustrating an image of a process to be executed by the control unit 40. The control unit 40 executes a predetermined computer program to realize the process shown in FIG. 3 and FIGS. 4A to 4C.

The control unit 40 sets a plurality of provisional set-points for the thickness and inner charge amount of an insulator film as those for obtaining a plurality of the theoretical surface voltage characteristics (Step S1. Provisional setting step, provisional setting unit). Parameters for determining the provisional set-points for the thickness and inner charge amount include a thickness median, a thickness range, a thickness step value, an inner charge amount median, an inner charge amount range and an inner charge amount step value. The thickness median is a median of a plurality of the thickness values provisionally set. The thickness range is a parameter for determining the range of the thickness values provisionally set. A plurality of the thickness values are provisionally set in a range between the value obtained by adding the thickness range to the thickness median, and the value obtained by subtracting the thickness range from the thickness median. The thickness step value is a parameter for defining an interval between the plurality of the thickness values to be provisionally set. That is, the plurality of the thickness values are provisionally set at intervals of the thickness step value. Similarly, the inner charge amount median is a median of a plurality of inner charge amount provisionally set. The inner charge amount range is a parameter for determining the range of the inner charge amounts provisionally set. That is, a plurality of the inner charge amounts are provisionally set in a range between the value obtained by adding the inner charge amount range to the inner charge amount median, and the value obtained by subtracting the inner charge amount range from the inner charge amount median. The inner charge amount step value is a parameter for defining an interval between the plurality of the inner charge amounts provisionally set, and the plurality of the inner charge amounts are provisionally set at intervals of the inner charge amount step value.

When the Step S1 processing is first executed, the control unit 40 sets the thickness and inner charge amount estimated for an insulator film to be calculated as the thickness median and the inner charge amount median, respectively. For example, the thickness median of 500 nm, the thickness range of 500 nm, the thickness step value of 100 nm, and the inner charge amount median of $5 \times 10^{12}/\text{cm}^2$ are set as initial values. However, to increase the calculation speed, for example, the insulator film thickness is obtained according to the inclination of the surface voltage with respect to the surface charge amount in the accumulation or inversion state of the measured surface voltage characteristic, and the value thus obtained may be set as an initial thickness median.

With respect to all the combinations of each of the plurality of the thickness values and inner charge amounts provisionally set in the manner described above, the theoretical surface voltage characteristic is calculated according to the above formula (1) (Step S2: Theoretical surface voltage characteristic calculation step, theoretical surface voltage characteristic calculation unit). The theoretical surface voltage value is obtained by correlating with the surface charge amount (plot on a curve L11 in FIG. 4A) of which actual data exists in the measured surface voltage characteristic (curve L11 in FIG. 4A) (plot on a curve L12 in FIG. 4A). Here, the theoretical surface voltage is calculated with the surface voltage change due to a surface adsorbed substance $\phi_{org}=0$. A reference value is used as the semiconductor substrate dielectric constant $\in_s$, and a value previously input to the control unit 40 is used as the substrate carrier concentration. Also, a reference value or the like may be used as the dielectric constant $\in_{ins}$ of the insulator film.

Then, the control unit 40 compares all the theoretical surface voltage characteristics obtained at Step S2 with the measured surface voltage characteristics, and individually calculates the surface voltage change due to a surface adsorbed substance on an insulator film, with respect to all the theoretical surface voltage characteristics (Step S3: Surface voltage change operation step, surface voltage change operation unit).

It can be seen from the formula (1) that when the surface voltage change due to a surface adsorbed substance exists, the surface voltage of the insulator film is shifted by the surface voltage change due to a surface adsorbed substance $\phi_{org}$. At Step S2, the theoretical surface voltage $V_{surf}$ is obtained based on the surface voltage change $\phi_{org}=0$. Therefore, the theoretical surface voltage characteristic corresponding to the actual characteristic of an insulator film formed on a wafer W is deviated, with respect to the measured surface voltage characteristic, by the surface voltage change $\phi_{org}$ in the direction of the surface voltage coordinate axis. Thus, a surface voltage mean value (mean value of all plots) of the estimated surface voltage characteristics (curve L12 in FIG. 4A) is obtained, and a surface voltage mean value (mean value of all plots) of the measured surface voltage characteristics (curve L11 in FIG. 4A) is further obtained. A difference between these mean values is calculated, and the result is set as the surface voltage change $\phi_{org}$. The above operation is executed for all the estimated surface voltage characteristics.

The control unit 40 further calculates a fitting index Fit which represents the extent of matching the theoretical surface voltage characteristic with the measured surface voltage characteristic (Step S4: Deviation operation step, deviation operation unit). The fitting index Fit refers to the standard deviation σ of the surface voltage difference $\Delta V_{surf}$ obtained by subtracting the plotted values (surface voltage) corresponding to each of the theoretical surface voltage characteristic (curve L12) and the surface voltage change $\phi_{org}$ from the plotted value (surface voltage) of the measured surface voltage characteristic (curve L11) (see FIG. 4C). In other words, the theoretical surface voltage characteristic (curve L12) is corrected by the surface voltage change $\phi_{org}$, and the standard deviation σ of the measured surface voltage characteristic (curve L11) with respect to the theoretical surface voltage characteristic (curve L12' in FIG. 4B) thus corrected is obtained as the fitting index Fit. The fitting index Fit is obtained with respect to all the theoretical surface voltage characteristics. It can be said that the closer the fitting index Fit is to zero, the closer the provisional set-point which is set as a base of the operation for the theoretical surface voltage characteristic corresponding to the fitting index Fit is to a true value.

At the control unit 40, the minimum value (the minimum fitting index value) is obtained from among all the fitting index Fit values obtained for the plurality of the theoretical surface voltage characteristics. Then, there are determined the set thickness and the set inner charge amount, each corresponding to the minimum fitting index value thus obtained (Step S5: Minimum deviation set-point determining step, minimum deviation set-point determining unit).

Thereafter, the control unit 40 judges whether or not the sequence of Steps S1 to S5 has been repeated a predetermined number of times (Step S6). If the number of repeated sequences has not reached the predetermined number, the sequence is then repeated from Step S1.

At this time, at Step S1, the control unit 40 sets the thickness value and the inner charge amount obtained at the previous Step S5, as a thickness median and an inner charge amount median, respectively. Also, as to the thickness range, thickness step value, inner charge amount range and inner charge amount step value, there is used a value obtained by multiplying by a predetermined coefficient α (<1), each of the thickness range, thickness step value, inner charge amount range and inner charge amount step value used in the previous Step S1 processing. The coefficient α is, for example, set to be α=0.1. This enables a detailed provisional setting of the thickness and inner charge amount in a range with high probability that a true value exists therein. Thus, by executing the subsequent processing steps from S2 to S5, there can be obtained the thickness and inner charge amount values more approximate to the true values thereof.

When the number of repeated sequences reaches the predetermined number, there is obtained the surface voltage change $\phi_{org}$ corresponding to the theoretical surface voltage characteristic which minimizes the fitting index Fit in the previous Step S5 processing (Step S7: Surface voltage change extracting step). In addition to the thickness value and inner charge amount obtained at the previous Step S5, the surface voltage change is output as a characteristic value (true value) representing the actual characteristic of an insulator film on a wafer W (Step S8).

Figure 5:
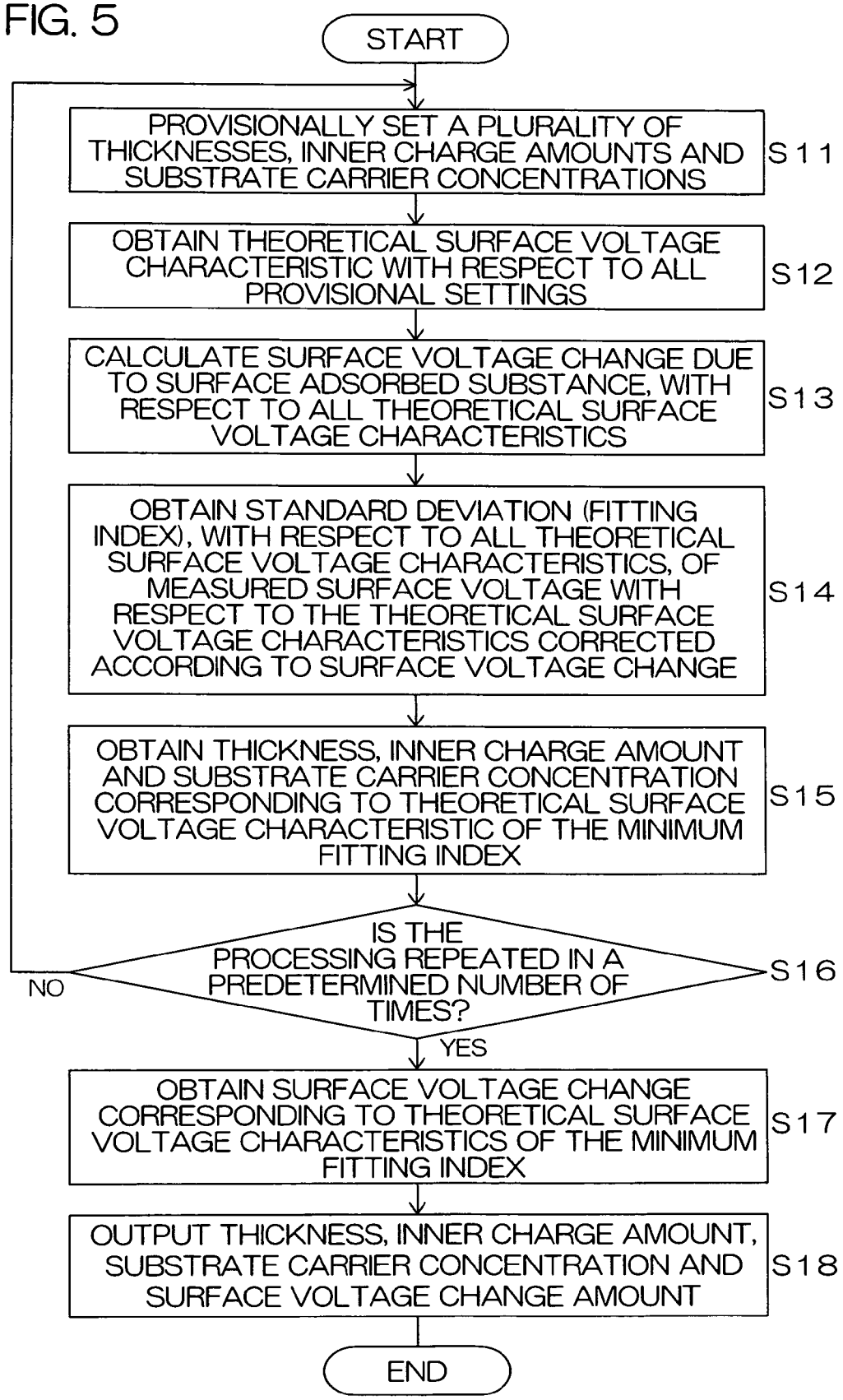
FIG. 5 is a flow chart for explaining another example of a process to be executed by a control unit, the flow chart illustrating a process in the case where the substrate carrier concentration is not known as well as the thickness, the inner charge amount and the surface voltage change due to a surface adsorbed substance.

FIG. 5 is a flow chart for explaining another example of a process to be executed by a control unit 40 when the characteristics of an insulator film formed on a wafer W are obtained, with the use of the measured surface voltage characteristic and a large number of theoretical surface voltage characteristics, the flow chart illustrating a process in the case where the substrate carrier concentration is not known as well as the thickness, the inner charge amount and the surface voltage change due to a surface adsorbed substance. In this FIG. 5, each of the steps corresponding to those shown in FIG. 3 is indicated with the number obtained by adding "10" to the step number shown in FIG. 3.

In this example, the control unit 40 sets, in addition to the thickness and inner charge amount of an insulator film, a plurality of provisional set-points for the substrate carrier concentration as those for obtaining a plurality of the theoretical surface voltage characteristics (Step S11). Parameters for determining the provisional set-points for the substrate carrier concentration as well as the thickness and inner charge amount include a thickness median, a thickness range, a thickness step value, an inner charge amount median, an inner charge amount range, an inner charge amount step value, a substrate carrier concentration median, a substrate carrier concentration range and a substrate carrier concentration step value. The provisional set-points for the thickness and inner charge amount are determined in the same manner as the processing in FIG. 3. The substrate carrier concentration median is a median of a plurality of the substrate carrier concentration values provisionally set. The substrate carrier concentration range is a parameter for determining the range of the substrate carrier concentration provisionally set. A plurality of the substrate carrier concentrations are provisionally set in the range between the value obtained by adding the substrate carrier concentration range to the substrate carrier concentration median, and the value obtained by subtracting the substrate carrier concentration range from the substrate carrier concentration median.

When the Step S11 processing is first executed, the control unit 40 sets the thickness and inner charge amount estimated for an insulator film to be calculated as the thickness median and the inner charge amount median, respectively. At the same time, the control unit 40 sets the substrate carrier concentration estimated for the substrate (wafer W) to be calculated as the substrate carrier concentration median. In the Step S11 processing during each repeated sequence, the control unit 40 uses the thickness, inner charge amount and substrate carrier concentration obtained at the previous Step S15 (to be discussed later) as the medians thereof. Furthermore, in the same manner as the above-described processing in FIG. 3, the thickness range, the thickness step value, the inner charge amount range, the inner charge amount step value, the substrate carrier concentration range and the substrate carrier concentration step value are determined by multiplying each of the ranges and step values used in the previous Step S11 processing, by α (α<1. e.g., α=0.1). Thus, by the repetitive processing, the precision of the calculated values for the thickness, inner charge amount and substrate carrier concentration can be gradually improved.

At Step S12, the control unit 40 operates such that the theoretical surface voltage characteristic is obtained with respect to all the combinations of each of the plurality of the thicknesses, inner charge amounts and substrate carrier concentrations provisionally set. Then, with respect to all the theoretical surface voltage characteristics thus obtained, there is obtained a difference between a mean value of the theoretical surface voltage characteristics and a mean value of the measured surface voltage characteristics, and the difference is assumed to be a surface voltage change due to a surface adsorbed substance adsorbed on the insulator film surface (Step S13).

At Step S14, the control unit 40 operates such that the fitting index Fit is obtained based on each of the theoretical surface voltage characteristics and the surface voltage change obtained corresponding thereto. The process for obtaining the fitting index Fit is the same as the above-described processing in FIG. 3.

At Step S15, the control unit 40 operates such that there are obtained the thickness, inner charge amount and substrate carrier concentration each corresponding to the theoretical surface voltage characteristic which minimizes the fitting index.

The processing at these steps changes each median of the thickness, inner charge amount and substrate carrier concentration. Further, the processing sequence is repeated a predetermined number of times, with reducing the ranges and step values of the provisional set-points thereof (Step S16).

When the theoretical surface voltage characteristic which minimizes the fitting index Fit is found by repeating the sequence the predetermined number of times, its corresponding surface voltage change is obtained (Step S17). Then, the values of the thickness, inner charge amount and substrate carrier concentration obtained in the last Step S15 processing and the value of the surface voltage change obtained in the Step S17 processing are output as values representing the wafer W characteristics (Step S18).

Accordingly, in the processing shown in FIG. 5, in addition to the values of the thickness, inner charge amount and surface voltage change (only due to a surface adsorbed substance) of an insulator film formed on a wafer W, the substrate carrier concentration can also be measured.

Figure 6:
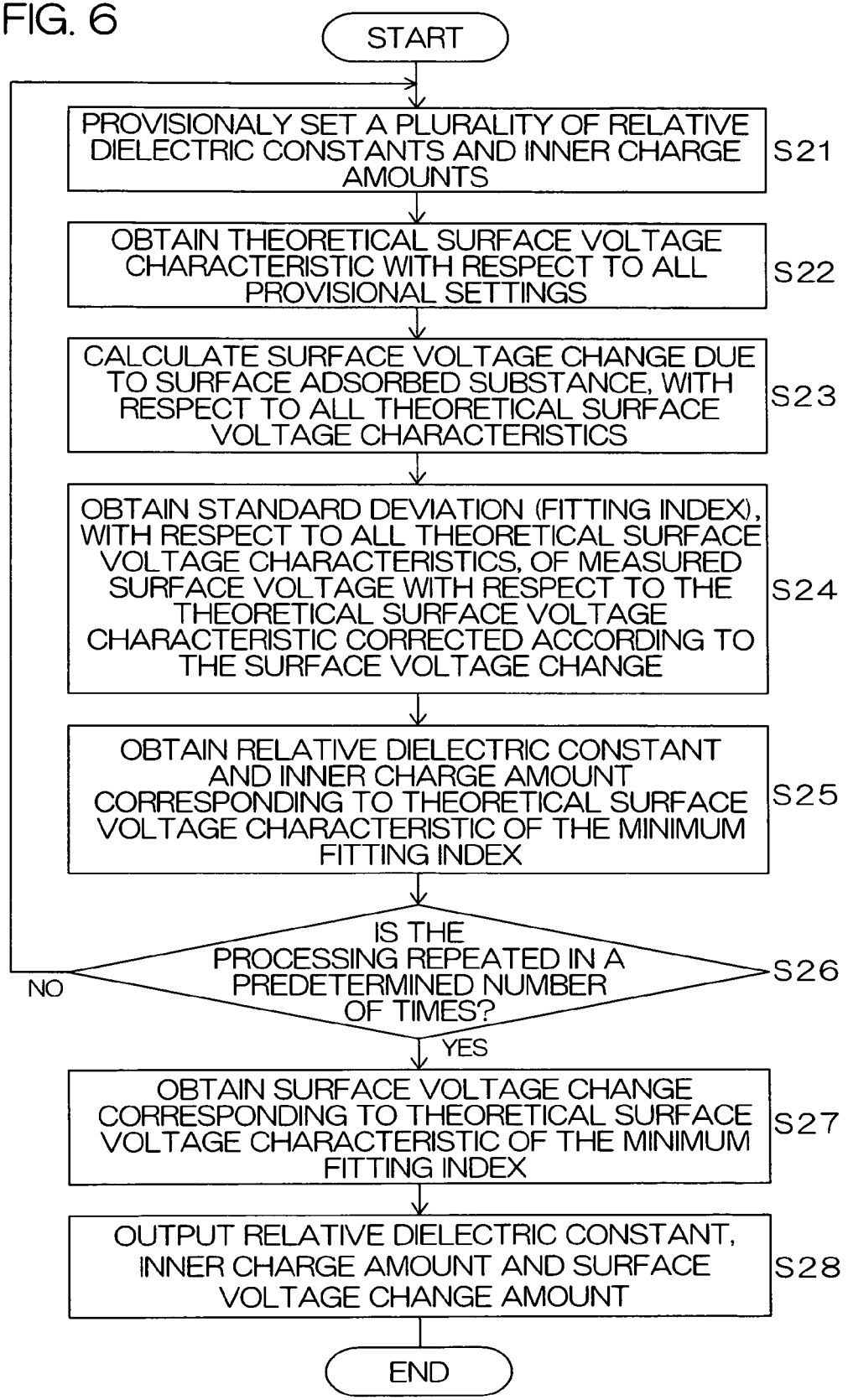
FIG. 6 is a flow chart for explaining another example of a process to be executed by a control unit, the flow chart illustrating a process in the case where the thickness of the insulator film is known but the relative dielectric constant, the inner charge amount and the surface voltage change due to a surface adsorbed substance are not known.

FIG. 6 is a flow chart for explaining another example of a processing to be executed by a control unit 40 when the characteristics of an insulator film formed on a wafer W are obtained, with the use of the measured surface voltage characteristic and a large number of theoretical surface voltage characteristics, the flow chart illustrating a process in the case where the thickness of the insulator film is known but the relative dielectric constant, the inner charge amount and the surface voltage change due to a surface adsorbed substance are not known. In the FIG. 6, each of the steps corresponding to those shown in FIG. 3 is indicated with the number obtained by adding "20" to the step number shown in FIG. 3.

For example, the insulator film thickness is previously obtained separately by an optical method (e.g., ellipsometry) or the like. More specifically, when the insulator film is a common gate insulator film, the insulator film thickness is relatively large and the relative dielectric constant is large. The thickness of the insulator film having such large thickness can be accurately measured by an optical method. Accordingly, by previously measuring the film thickness separately with a thickness measuring apparatus which utilizes the optical principle, the relative dielectric constant of an insulator film can be calculated with the measured value.

The control unit 40 determines a plurality of provisional set-points for the relative dielectric constant and inner charge amount of an insulator film as provisional set-points for obtaining a plurality of the theoretical surface voltage characteristics (Step S21). Parameters for determining the provisional set-points for the relative dielectric constant and inner charge amount include a relative dielectric constant median, a relative dielectric constant range, a relative dielectric constant step value, an inner charge amount median, an inner charge amount range and an inner charge amount step value. The provisional set-point for the inner charge amount can be determined in the same manner as the processing in FIG. 3. The relative dielectric constant median is a median of a plurality of the relative dielectric constants provisionally set. The relative dielectric constant range is a parameter for determining the range of the relative dielectric constant provisionally set. A plurality of the relative dielectric constants are provisionally set in the range between the value obtained by adding the relative dielectric constant range to the relative dielectric constant median, and the value obtained by subtracting the relative dielectric constant range from the relative dielectric constant median.

When the Step S21 processing is first executed, the control unit 40 sets the relative dielectric constant and inner charge amount estimated for an insulator film to be calculated, as the relative dielectric constant median and the inner charge amount median, respectively. In the Step S21 processing during each repeated sequence, the control unit 40 uses the relative dielectric constant and inner charge amount obtained at the previous Step S25 (to be discussed later) as the medians thereof. Furthermore, in the same manner as the above-described processing in FIG. 3, the relative dielectric constant range, the relative dielectric constant step value, the inner charge amount range and the inner charge amount step value are determined by multiplying each of the ranges and step values used in the previous Step S21 processing, by $\alpha$ ($\alpha<1$. e.g., $\alpha=0.1$). Thus, by the repetitive processing, the precision of the calculated values for the relative dielectric constant and inner charge amount can be gradually improved.

At Step S22, the control unit 40 operates such that the theoretical surface voltage characteristic is obtained with respect to all the combinations of each of the plurality of the relative dielectric constants and inner charge amounts provisionally set. Then, with respect to all the theoretical surface voltage characteristics thus obtained, there is obtained a difference between a mean value of the theoretical surface voltage characteristics and a mean value of the measured surface voltage characteristics, and the difference is assumed to be a surface voltage change due to a surface adsorbed substance adsorbed on the insulator film surface (Step S23).

At Step S24, the control unit 40 operates such that the fitting index Fit is obtained based on each of the theoretical surface voltage characteristics and surface voltage change obtained corresponding thereto. The processing for obtaining the fitting index Fit is the same as the above-described processing in FIG. 3.

At Step S25, the control unit 40 operates such that there are obtained the relative dielectric constant and inner charge amount each corresponding to the theoretical surface voltage characteristic which minimizes the fitting index.

The processing at these steps changes each median of the relative dielectric constant and inner charge amount. Further, the processing sequence is repeated a predetermined number of times, with reducing the ranges and step values of the provisional set-points thereof by the coefficient $\alpha$ (Step S26).

When the theoretical surface voltage characteristic which minimizes the fitting index Fit is found by repeating the sequence the predetermined number of times, its corresponding surface voltage change is obtained (Step S27). Then, the values of the relative dielectric constant and inner charge amount obtained in the last Step S25 processing and the value of the surface voltage change obtained in the Step S27 processing are output as values representing the wafer W characteristics (Step S28).

Accordingly, in the processing shown in FIG. 6, there can be measured the values of the relative dielectric constant, inner charge amount and surface voltage change (only due to a surface adsorbed substance) of an insulator film formed on a wafer W.

Figure 7:
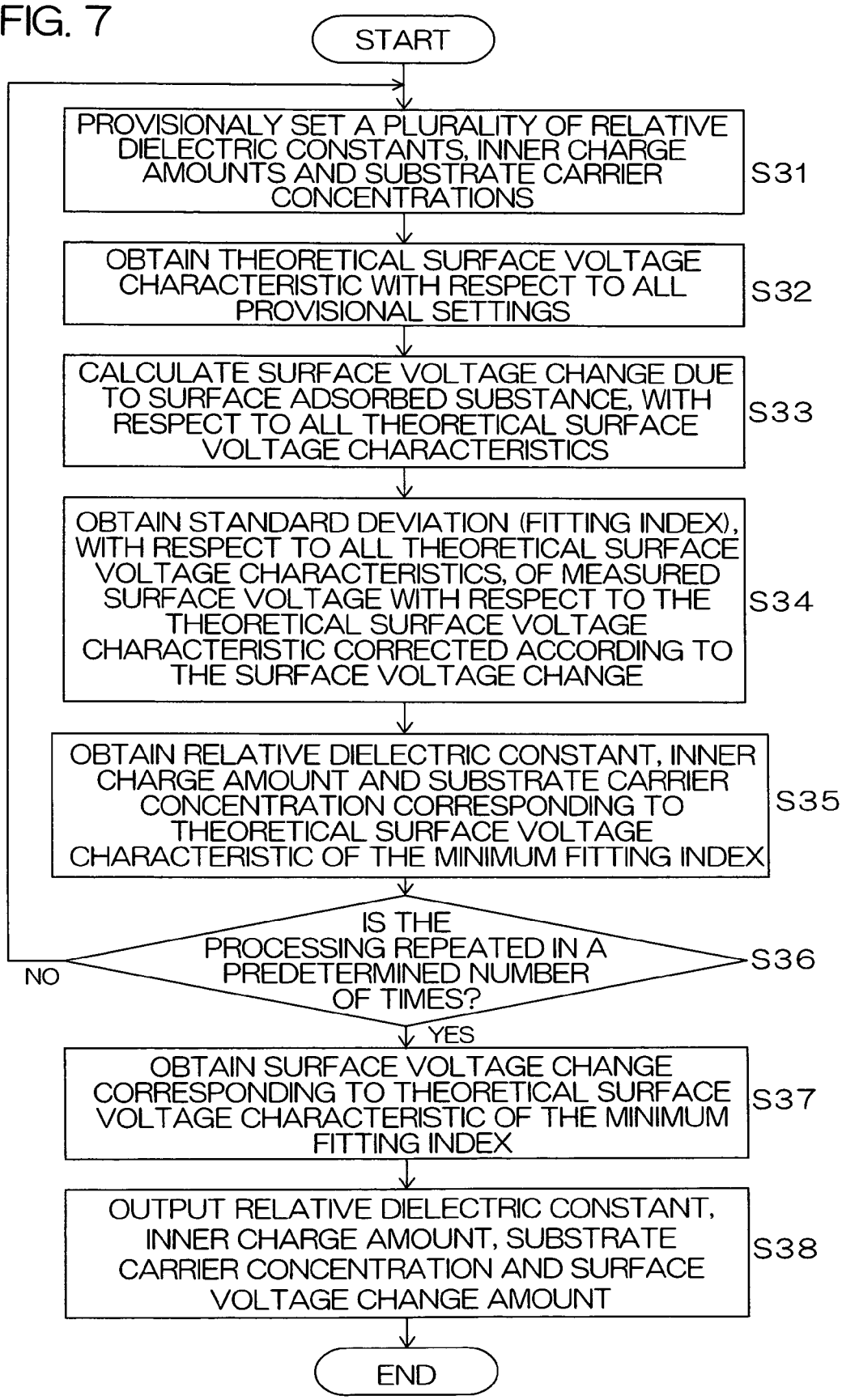
FIG. 7 is a flow chart for explaining a still further another example of a process to be executed by a control unit, the flow chart illustrating a process in the case where the thickness of an insulator film is known but the relative dielectric constant, the inner charge amount and the substrate carrier concentration, and the surface voltage change due to a surface adsorbed substance are not known.

The processing in FIG. 6 can also be transformed as in the processing in FIG. 5, and thus the substrate carrier concentration can be additionally obtained. The processing by the control unit 40 in such case is shown in FIG. 7. In the FIG. 7, each of the steps corresponding to those shown in FIG. 6 is indicated with the number obtained by adding "10" to the step numbers shown in FIG. 6.

In this example, the control unit 40 sets, in addition to the relative dielectric constant and inner charge amount of an insulator film, a plurality of provisional set-points for the substrate carrier concentration as those for obtaining a plurality of the theoretical surface voltage characteristics (Step S31). Parameters for determining the provisional set-points for the substrate carrier concentration as well as the relative dielectric constant and inner charge amount include a relative dielectric constant median, a relative dielectric constant range, a relative dielectric constant step value, an inner charge amount median, an inner charge amount range, an inner charge amount step value, a substrate carrier concentration median, a substrate carrier concentration range and a substrate carrier concentration step value.

When the Step S31 processing is first executed, the control unit 40 sets the relative dielectric constant and inner charge amount estimated for an insulator film to be calculated, as the relative dielectric constant median and an inner charge amount median, respectively. At the same time, the control unit 40 sets the substrate carrier concentration estimated for the substrate (wafer W) to be calculated as the substrate carrier concentration median. In the Step S31 processing during each repeated sequence, the control unit 40 uses the relative dielectric constant, inner charge amount and substrate carrier concentration obtained at the previous Step S35 (to be discussed later) as medians thereof. Furthermore, in the same manner as the above-described processing in FIG. 6, the relative dielectric constant range, the relative dielectric constant step value, the inner charge amount range, the inner charge amount step value, the substrate carrier concentration range and the substrate carrier concentration step value are determined by multiplying each of the ranges and step values used in the previous Step S31 processing, by $\alpha$ ($\alpha<1$. e.g., $\alpha=0.1$). Thus, by the repetitive processing, the calculation precision of the relative dielectric constant, inner charge amount and substrate carrier concentration is gradually improved.

At Step S32, the control unit 40 operates such that the theoretical surface voltage characteristic is obtained with respect to all the combinations of each of the plurality of the relative dielectric constants, inner charge amounts and substrate carrier concentrations provisionally set. Then, with respect to all the theoretical surface voltage characteristics thus obtained, there is obtained a difference between a mean value of the theoretical surface voltage characteristics and a mean value of the measured surface voltage characteristics, and the difference is assumed to be a surface voltage change due to a surface adsorbed substance adsorbed on the insulator film surface (Step S33).

At Step S34, the control unit 40 operates such that the fitting index Fit is obtained based on each of the theoretical surface voltage characteristics and the surface voltage change obtained corresponding thereto. The process for obtaining the fitting index Fit is the same as the above-described processing in FIG. 3.

At Step S35, the control unit 40 operates such that there are obtained the relative dielectric constant, inner charge amount and substrate carrier concentration each corresponding to the theoretical surface voltage characteristic which minimizes the fitting index.

The processing at these steps change each median of the relative dielectric constant, inner charge amount and substrate carrier concentration. Further, the processing sequence is repeated a predetermined number of times, with reducing the ranges and step values of the provisional set-points thereof (Step S36).

When the theoretical surface voltage characteristic which minimizes the fitting index Fit is found by repeating the sequence the predetermined number of times, its corresponding surface voltage change is obtained (Step S37). Then, the values of the relative dielectric constant, inner charge amount and substrate carrier concentration obtained in the last Step S35 processing and the value of the surface voltage change obtained in the Step S37 processing are output as values representing the wafer W characteristics (Step S38).

Accordingly, in the processing shown in FIG. 7, in addition to the values of the relative dielectric constant, inner charge amount and surface voltage change (only due to a surface adsorbed substance) of an insulator film formed on a wafer W, the substrate carrier concentration can also be measured.

In the processing examples discussed above, the case where either the thickness or relative dielectric constant of an insulator film is not known is discussed. On the other hand, in the case where both the thickness and relative dielectric constant of an insulator film are known by the reference or the like, provisional set-points are not determined for the film thickness or relative dielectric constant, but a plurality of provisional set-points may be determined only for the inner charge amount, or only for the inner charge amount and substrate carrier concentration, to execute similar processing. This can simplify the processing to be executed by the control unit 40. Under the simplified processing, there can be obtained the inner charge amount and surface voltage change due to a surface adsorbed substance (in addition, the substrate carrier concentration in the case of determining provisional set-points for the substrate carrier concentration).

At the Steps S1, S11, S21 and S31 described above, each median of the film thicknesses or the like is modified to the values obtained at Steps S5, S15, S25 and S35. The medians at the time of determining the provisional set-points may be previously recorded in a program to be executed by the control unit 40 or in a storage medium or the like (not shown) provided in the control unit 40, so that the values obtained according to the number of repeat sequences may be read for use.

The following outlines the processing to be executed by the control unit 40 for the calculation of the charge amount on the insulator film surface according to the C-V measurement.

Figure 8:
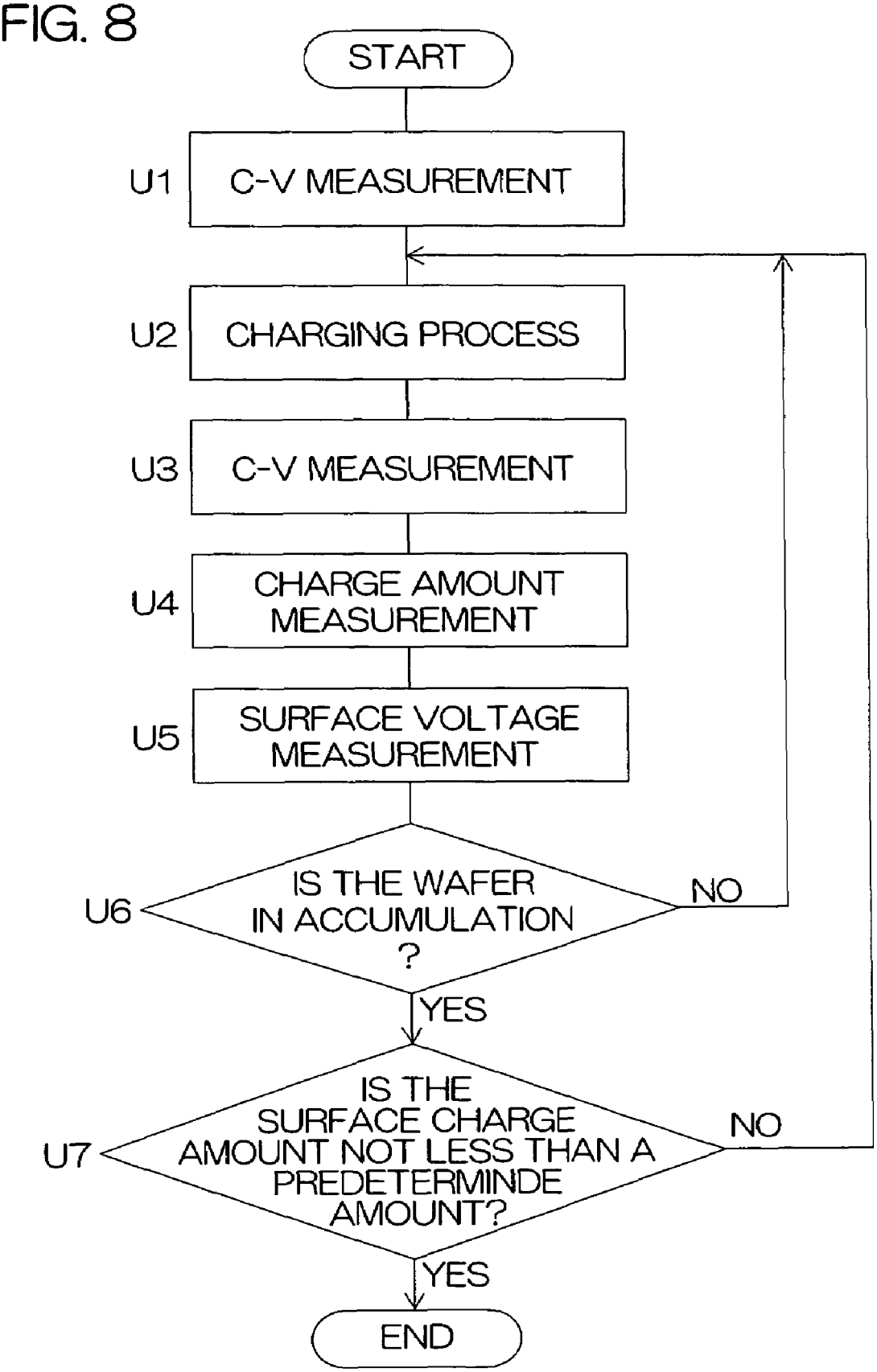
FIG. 8 is a flow chart for explaining a process to be executed by a control unit at the time when the surface voltage characteristic (measured surface voltage characteristic) with respect to the surface charge amount of an insulator film formed on a surface of a wafer by the insulator film characteristic measuring apparatus in FIG. 1 is measured.

FIG. 8 is a flow chart for explaining a processing to be executed by a control unit 40 at the time when the surface voltage characteristic (measured surface voltage characteristic) with respect to the surface charge amount of an insulator film formed on a surface of a wafer W by the insulator film characteristic measuring apparatus 20 in FIG. 1 is measured.

First held on the holding stand 5 is a wafer W with its surface having an insulator film formed thereon being turned up. The control unit 40 controls the moving mechanism 7 to move the wafer W to a C-V measuring position. Then, the control unit 40 operates such that while the gap $d_{air}$ based on the output signal of the light amount measuring device 29 is monitored, the stepping motor 22 and the piezoelectric actuator 23 are controlled to adjust the gap $d_{air}$ to a predetermined value.

Then, the control unit 40 controls the impedance meter 26 to conduct a C-V measurement in which a combined capacitance between the holding stand 5 and the measuring electrode 21 at each bias voltage is measured (Step U1). At this time, the C-V measurement is conducted in a non-contact manner with respect to the wafer W because the wafer W is disposed with a gap provided with respect to the measuring electrode 21. Thus, there is obtained a C-V curve CV1 representing the relationships between the bias voltage and the combined capacitance.

Figure 9:
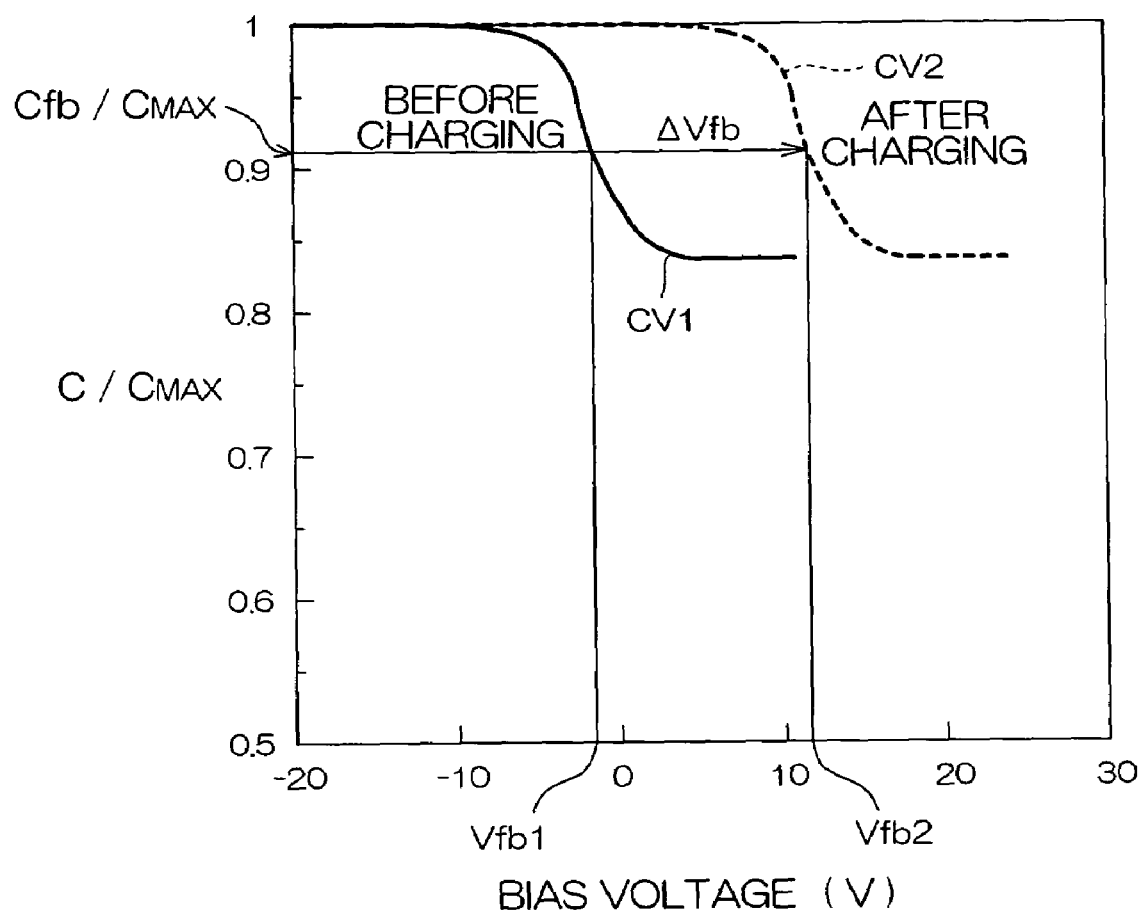
FIG. 9 is a view for explaining a C-V measurement.

FIG. 9 shows an example of the C-V curve. In FIG. 9, the axis of abscissa shows a bias voltage, while the axis of ordinates shows a value obtained by standardizing a combined capacitance C by a maximum combined capacitance $C_{MAX}$ (hereinafter referred to as "a standardized capacitance"). The standardized capacitance $C/C_{MAX}$ converges on 1 in the negative side of the bias voltage. With an increase in bias voltage, the standardized capacitance $C/C_{MAX}$ is reduced, and remarkably reduced at a certain bias voltage. By the operation of the control unit 40, a first flat band voltage $V_{fb1}$ is obtained from the C-V curve.

This operation is detailed in the MOS Physics and Technology, P487 (published by WILEY-INTERSCIENCE PUBLICATION in 1982). First, a flat band capacitance $C_{fb}$ corresponding to the first flat band voltage $V_{fb1}$ is obtained according to the following formula (8):

$$C_{fb} = C_{fbs}C_{MAX}/(C_{MAX}+C_{fbs}) \quad (8)$$

where $C_{fbs}$ is the flat band capacitance of silicon (wafer W) and is expressed by the following formula (9):

$$C_{fbs} = \epsilon_s/\lambda_p \quad (9)$$

where $\epsilon_s$ is the dielectric constant of the wafer W and is equal to the product of the dielectric constant $\epsilon_o$ in a vacuum and the relative dielectric constant $\epsilon_{Si}$ of the wafer W. A reference value or the like may be used as the relative dielectric constant $\epsilon_{Si}$ of the wafer W. In the formula (9), $\lambda_p$ is a Debye length and is expressed by the following formula (10):

$$\lambda_p = \{(kT\epsilon_o\epsilon_{Si})/(q_o^2 N_d)\}^{1/2} \quad (10)$$

where k is a Boltzmann constant, $q_o$ is an elementary charge, T is the temperature of the semiconductor wafer W and may be substituted by the temperature in the chamber 9 measured by the temperature sensor 10, and $N_d$ is the carrier concentration of the wafer W which can be obtained by measurement separately as required. The carrier concentration $N_d$ is generally measured at the time when the wafer W is purchased. Accordingly, this measured value can also be used. The carrier concentration $N_d$ can also be obtained according to the inclination of the C-V curve.

When the flat band capacitance $C_{fb}$ is obtained in the manner mentioned above, the first flat band voltage $V_{fb1}$ is obtained as the value of the bias voltage at which the standardized capacitance $C/C_{MAX}$ is equal to $C_{fb}/C_{MAX}$ in the C-V curve CV1 (See FIG. 9).

Then, the control unit 40 controls the moving mechanism 7 to move the wafer W to the charging processing position. The control unit 40 controls the direct current power supply 8 to apply a predetermined voltage between the needle 11 and the holding stand 5. This generates corona discharge between the needle 11 and the wafer W, causing the insulator film formed on the wafer W surface to be uniformly charged (Step U2).

At this time, the control unit 40 controls the polarity of the direct current power supply 8 based on the information as to the conduction type of the wafer W previously given to the control unit 40. That is, the insulator film surface is negatively charged when the wafer W is a P-type semiconductor, and the insulator film surface is positively charged when the wafer W is an N-type semiconductor.

Then, the control unit 40 controls the moving mechanism 7 to move the wafer W to the C-V measuring position where a C-V measurement is conducted (Step U3). At this time, the magnitude of the gap $d_{air}$ is set substantially equal to that at the time of the C-V measurement at Step U1. Thus, a C-V curve CV2 after the charging processing is obtained (See FIG. 9). The C-V curve CV2 after the charging processing has a shape as if obtained by shifting the C-V curve CV1 before the charging processing in the positive direction of the bias voltage coordinate axis.

Then, by the operation of the control unit 40, a flat band voltage (second flat band voltage) $V_{fb2}$ after the charging processing is obtained from the C-V curve CV2.

The second flat band voltage $V_{fb2}$ is obtained as the value of the bias voltage at which the standardized capacitance $C/C_{MAX}$ is equal to $C_{fb}/C_{MAX}$ in the C-V curve CV2 (See FIG. 9).

By the operation of the control unit 40, a charge amount Q given to the wafer W surface by the charging processing is obtained, according to the following formula (11), with the use of a difference $\Delta V_{fb}$ between the second flat band voltage $V_{fb2}$ and the first flat band voltage $V_{fb1}$, and of the gap $d_{air}$ (Step U4):

$$\Delta V_{fb} = -Q d_{air}/\epsilon_o \quad (11)$$

Then, the control unit 40 controls the moving mechanism 7 to move the wafer W to the surface voltage measuring position where the surface voltage $V_{surf}$ of the wafer W is measured (Step U5). Thus, there is obtained a set of data comprising the charge amount Q and the surface voltage $V_{surf}$ thereat. The C-V measurement (Step U3) and the surface voltage $V_{surf}$ measurement (Step U5) are conducted within a period of time during which the charge amount Q of the insulator film surface can be regarded as unchanged.

Then, the control unit 40 judges whether or not the wafer W is in accumulation, i.e., whether or not the combined capacitance C substantially undergoes no change in the vicinity of the zero bias in the C-V curve (Step U6). For example in FIG. 9, the wafer W according to the C-V curve CV1 is not in accumulation, while the wafer W according to the C-V curve CV2 is in accumulation.

When the wafer W is not in accumulation (NO at Step U6), the process is returned to Step U2. Then, there are successively conducted a charging processing (Step U2), a C-V measurement (Step U3), a charge amount Q calculation (Step U4), and a surface voltage $V_{surf}$ measurement (Step U5). By the charging processing on and after the second time, the insulator film surface is successively greatly charged negatively when the wafer W is a P-type semiconductor, and the insulator film surface is successively greatly charged positively when the wafer W is an N-type semiconductor.

In the charge amount Q calculation (Step U4), the value obtained by the C-V measurement (Step U1) before the first charging processing, is used as the first flat band voltage $V_{fb1}$, and the value obtained by the just previous C-V measurement (after the previous charging processing) is used as the second flat band voltage $V_{fb2}$ (also applied thereafter).

Each time Step U2 to Step U5 are executed, there are increased data sets, each comprising a charge amount Q and the surface voltage $V_{surf}$ thereat.

As to the measured surface voltage characteristic to be obtained, it is desirable that there exist the accumulation and depletion states or the accumulation, depletion and inversion states in the measured surface voltage characteristics.

When the wafer W is in accumulation (YES at Step U6), it is judged whether or not the charge amount Q is not less than a predetermined amount (Step U7). When the charge amount Q is extremely large, it is always judged that, within the range of a bias voltage which can be applied by the impedance meter 26, the wafer W only shows it is in accumulation (in which the C-V curves CV1, CV2 in FIG. 8 are shifted extremely in the positive direction of the bias voltage coordinate axis). Accordingly, the flat band voltage cannot be obtained. The predetermined value of the charge amount Q is set such that it can be judged whether or not the flat band voltage of the wafer W can be obtained by a C-V measurement.

When the charge amount Q is smaller than the predetermined value (NO at Step U7), there is a chance that a C-V measurement is further conducted to obtain a flat band voltage. Accordingly, the process is returned to Step U2, and there are executed a charging processing (Step U2), a C-V measurement (Step U3), a charge amount Q calculation (Step U4), a surface voltage $V_{surf}$ measurement (Step U4) and judgment whether or not the wafer W is in accumulation (Step U6).

When the charge amount Q is not less than the predetermined value (YES at Step U7), the measurement of the surface voltage characteristic is completed. Thus, there can be obtained a surface voltage $V_{surf}$ change (surface voltage characteristic) with respect to the charge amount Q.

In the foregoing, an embodiment of the present invention has been discussed, but the present invention can also be further embodied in a different manner. For example, in the embodiment described above, the theoretical surface voltage characteristic is obtained with respect to all the combinations of the provisional set-points (Steps S2, S12, S22, and S32), and thereafter, the surface voltage change (Steps S3, S13, S23, and S33) and the fitting index (Steps S4, S14, S24, and S34) are obtained with respect to all the theoretical surface voltage characteristics thus obtained. However, there may be a calculation sequence such that each time one theoretical surface voltage characteristic is obtained, the surface voltage change and the fitting index are obtained with respect to the theoretical surface voltage characteristic thus obtained.

Further, in the embodiment described above, the arrangement of charging an insulator film on the wafer W surface by corona discharge is explained. However, for example, an ultraviolet ray (UV) irradiation unit may be disposed, instead of the charging processing unit 1 shown in FIG. 1, such that an insulator film on the wafer W surface is charged by irradiating ultraviolet rays (for example, having a wavelength of not less than 220 nm and not greater than 300 nm) to the wafer W.

Embodiments of the present invention have been discussed in detail, but these embodiments are mere specific examples for clarifying the technical contents of the present invention. Therefore, the present invention should not be construed as limited to these specific examples. The spirit and scope of the present invention are limited only by the appended claims.

This Application corresponds to Japanese Patent Application Serial No. 2005-376174 filed on Dec. 27, 2005 with Japanese Patent Office, the disclosure of which is incorporated herein by reference.

What is claimed is:

1. An insulator film characteristic measuring method for measuring the characteristics of an insulator film formed on a surface of a semiconductor substrate in a non-contact manner with respect to the insulator film, comprising:

a surface voltage characteristic measuring step of measuring a measured surface voltage characteristic which is a surface voltage characteristic with respect to a surface charge amount of the insulator film in a non-contact manner with respect to the insulator film;

a provisional setting step of provisionally setting a plurality of inner charge amounts;

a theoretical surface voltage characteristic calculation step of calculating, with respect to each of the plurality of inner charge amounts provisionally set, a theoretical surface voltage characteristic which is a theoretical characteristic of the surface voltage with respect to the surface charge amount of the insulator film;

a step of obtaining, with respect to each of the theoretical surface voltage characteristics, a mean value difference which is a difference between a surface voltage mean value obtained based on the measured surface voltage characteristics and a surface voltage mean value obtained based on the theoretical surface voltage characteristics, so that the mean value difference is set as a surface voltage change due to a surface adsorbed substance which is adsorbed on the insulator film surface;

a step of calculating, with respect to each of the theoretical surface voltage characteristics, a deviation of the measured surface voltage characteristic with respect to a corrected surface voltage characteristic which is obtained by correcting the theoretical surface voltage characteristic according to the surface voltage change; and a minimum deviation set-point determining step of determining a set-point for the inner charge amount corresponding to the theoretical surface voltage characteristic which minimizes the deviation.

2. An insulator film characteristic measuring method according to claim 1, wherein the provisional setting step includes a step of setting a plurality of thicknesses and inner charge amounts of the insulator film;

the theoretical surface voltage characteristic calculation step includes a step of calculating a theoretical surface voltage characteristic with respect to a plurality of combinations of each of the plurality of the thicknesses and inner charge amounts thus provisionally set; and the minimum deviation set-point determining step includes a step of determining a set-point group including a thickness and an inner charge amount, each corresponding to the theoretical surface voltage characteristic which minimizes the deviation.

3. An insulator film characteristic measuring method according to claim 1, wherein the provisional setting step includes a step of setting a plurality of the inner charge amounts and substrate carrier concentrations;

the theoretical surface voltage characteristic calculation step includes a step of calculating a theoretical surface voltage characteristic with respect to a plurality of combinations of each of the plurality of the inner charge amounts and substrate carrier concentrations thus provisionally set; and the minimum deviation set-point determining step includes a step of determining a set-point group including an inner charge amount and a substrate carrier concentration, each corresponding to the theoretical surface voltage characteristic which minimizes the deviation.

4. An insulator film characteristic measuring method according to claim 1, wherein
the provisional setting step includes a step of setting a plurality of thicknesses, inner charge amounts and substrate carrier concentrations of the insulator film;
the theoretical surface voltage characteristic calculation step includes a step of calculating a theoretical surface voltage characteristic with respect to a plurality of combinations of each of the plurality of the thicknesses, inner charge amounts and substrate carrier concentrations thus provisionally set; and
the minimum deviation set-point determining step includes a step of determining a set-point group comprising a thickness, an inner charge amount and a substrate carrier concentration, each corresponding to the theoretical surface voltage characteristic which minimizes the deviation.

5. An insulator film characteristic measuring method according to claim 1, wherein
the provisional setting step includes a step of setting a plurality of relative dielectric constants and inner charge amounts of the insulator film;
the theoretical surface voltage characteristic calculation step includes a step of calculating a theoretical surface voltage characteristic with respect to a plurality of combinations of each of the plurality of the relative dielectric constants and inner charge amounts thus provisionally set; and
the minimum deviation set-point determining step includes a step of determining a set-point group comprising a relative dielectric constant and an inner charge amount, each corresponding to the theoretical surface voltage characteristic which minimizes the deviation.

6. An insulator film characteristic measuring method according to claim 1, wherein
the provisional setting step includes a step of setting a plurality of relative dielectric constants, inner charge amounts and substrate carrier concentrations of the insulator film;
the theoretical surface voltage characteristic calculation step includes a step of calculating a theoretical surface voltage characteristic with respect to a plurality of combinations of each of the plurality of the relative dielectric constants, inner charge amounts and substrate carrier concentrations thus provisionally set; and
the minimum deviation set-point determining step includes a step of determining a set-point group comprising a relative dielectric constant, an inner charge amount and a substrate carrier concentration, each corresponding to the theoretical surface voltage characteristic which minimizes the deviation.

7. An insulator film characteristic measuring method according to claim 1, 2, 3, 4, 5, or 6, further comprising a step of extracting a surface voltage change obtained so as to correspond to the theoretical surface voltage characteristic associated with the set-points determined according to the minimum deviation set-point determining step.

8. An insulator film characteristic measuring apparatus for measuring the characteristics of an insulator film formed on a surface of a semiconductor substrate in a non-contact manner with respect to the insulator film, comprising:
a surface voltage characteristic measuring unit for measuring a measured surface voltage characteristic which is a surface voltage characteristic with respect to a surface charge amount of the insulator film in a non-contact manner with respect to the insulator film;
a provisional setting unit for provisionally setting a plurality of inner charge amounts;
a theoretical surface voltage characteristic calculation unit for calculating, with respect to each of the plurality of inner charge amounts provisionally set, a theoretical surface voltage characteristic which is a theoretical characteristic of the surface voltage with respect to the surface charge amount of the insulator film;
a surface voltage change operation unit for obtaining, with respect to each of the theoretical surface voltage characteristics, a mean value difference which is a difference between a surface voltage mean value obtained based on the measured surface voltage characteristics and a surface voltage mean value obtained based on the theoretical surface voltage characteristics, so that the mean value difference is set as a surface voltage change due to a surface adsorbed substance which is adsorbed on the insulator film surface;
a deviation operation unit for calculating, with respect to each of the theoretical surface voltage characteristics, a deviation of the measured surface voltage characteristic with respect to the corrected surface voltage characteristic which is obtained by correcting the theoretical surface voltage characteristic according to the surface voltage change; and
a minimum deviation set-point determining unit for determining a set-point for the inner charge amount corresponding to the theoretical surface voltage characteristic which minimizes the deviation.

* * * * *